United States Patent [19]
Yang et al.

[11] Patent Number: 5,824,352
[45] Date of Patent: Oct. 20, 1998

[54] APPARATUS FOR PRODUCING AN APERTURED PLASTIC FILM HAVING A TRICOT TEXTURE

[75] Inventors: Ching-Yun Morris Yang, Princeton Junction; Charles Shimalla, Plainsboro; Mordechai Turi, Princeton Junction, all of N.J.

[73] Assignee: McNeil-PPC, Inc., Skillman, N.J.

[21] Appl. No.: 747,937

[22] Filed: Nov. 12, 1996

Related U.S. Application Data

[63] Continuation of Ser. No. 307,973, Sep. 16, 1994, abandoned.

[51] Int. Cl.$^6$ .................................................. B26F 1/26
[52] U.S. Cl. .............. 425/290; 425/387.1; 425/DIG. 37; 425/DIG. 119; 264/504
[58] Field of Search ................ 425/290, 387.1, 425/326.1, DIG. 37, DIG. 119, 388; 264/504

[56] References Cited

U.S. PATENT DOCUMENTS

| | | | |
|---|---|---|---|
| 3,565,308 | 2/1971 | Slack | 264/DIG. 47 |
| 3,566,735 | 3/1971 | Greene | 264/DIG. 47 |
| 3,596,816 | 8/1971 | Brown | 264/DIG. 47 |
| 3,632,269 | 1/1972 | Doviak | 425/362 |
| 3,883,279 | 5/1975 | Heyer | 425/161 |
| 3,929,135 | 12/1975 | Thompson | 128/287 |
| 4,151,240 | 4/1979 | Lucas et al. | 264/504 |
| 4,272,473 | 6/1981 | Riemersma et al. | 264/154 |
| 4,287,249 | 9/1981 | Eustance et al. | 428/141 |
| 4,324,246 | 4/1982 | Mullane et al. | 128/287 |
| 4,324,276 | 4/1982 | Kemner | 138/30 |
| 4,377,544 | 3/1983 | Rasmussen | 264/DIG. 47 |
| 4,381,326 | 4/1983 | Kelly | 428/134 |
| 4,455,337 | 6/1984 | Lloyd et al. | 264/DIG. 47 |
| 4,509,908 | 4/1985 | Mullane, Jr. | 425/387.1 |
| 4,552,709 | 11/1985 | Koger, II et al. | 264/504 |
| 4,591,523 | 5/1986 | Thompson | 428/131 |
| 4,609,518 | 9/1986 | Curro et al. | 264/504 |
| 4,690,679 | 9/1987 | Mattingly, III et al. | 604/383 |
| 4,695,422 | 9/1987 | Curro et al. | 425/387.1 |
| 4,772,444 | 9/1988 | Curro et al. | 425/326.1 |
| 4,806,303 | 2/1989 | Bianco et al. | 264/504 |
| 4,839,216 | 6/1989 | Curro et al. | 428/134 |
| 5,098,764 | 3/1992 | Drelich et al. | 428/131 |
| 5,158,819 | 10/1992 | Goodman, Jr. et al. | 428/131 |
| 5,244,711 | 9/1993 | Drelich et al. | 428/113 |
| 5,269,981 | 12/1993 | Jameson et al. | 264/23 |
| 5,441,691 | 8/1995 | Dobrin et al. | 264/504 |

FOREIGN PATENT DOCUMENTS

| | | |
|---|---|---|
| 304617 | 9/1989 | European Pat. Off. . |
| WO 94/04112 | 3/1994 | WIPO . |

*Primary Examiner*—Catherine Timm

[57] ABSTRACT

An apparatus for producing an apertured plastic film having a tricot-like texture. The apparatus includes a film forming member comprising a rotatable hollow drum having a pattern of apertures and a topographical outer surface formed by a cluster of peaks and valleys surrounding each aperture. A plastic film is placed on the apices of the peaks and fluid streams are projected against the film while the drum is rotated. The fluid forces the film against the topographical outer surface of the drum causing the film to become apertured and to have a tricot-like texture corresponding to the pattern of apertures and peaks and valleys.

2 Claims, 8 Drawing Sheets

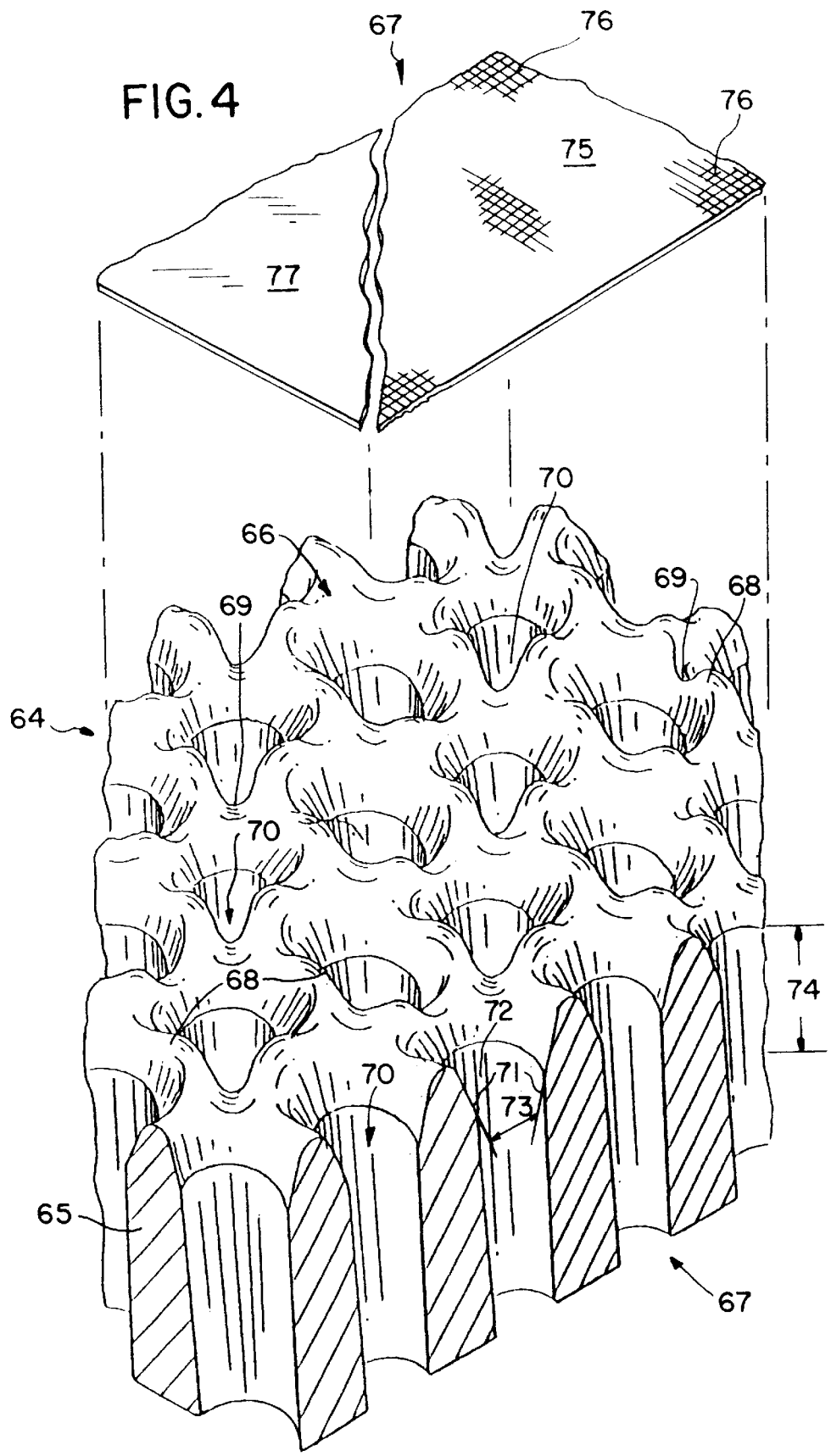

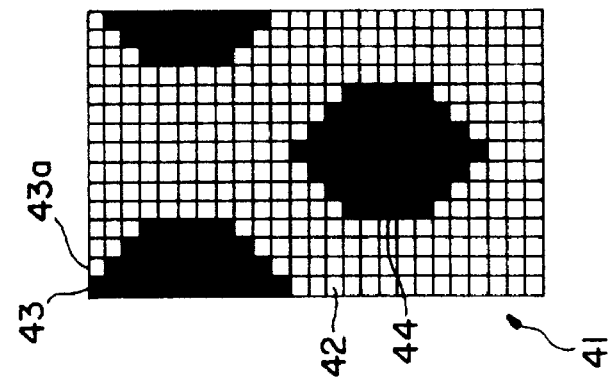
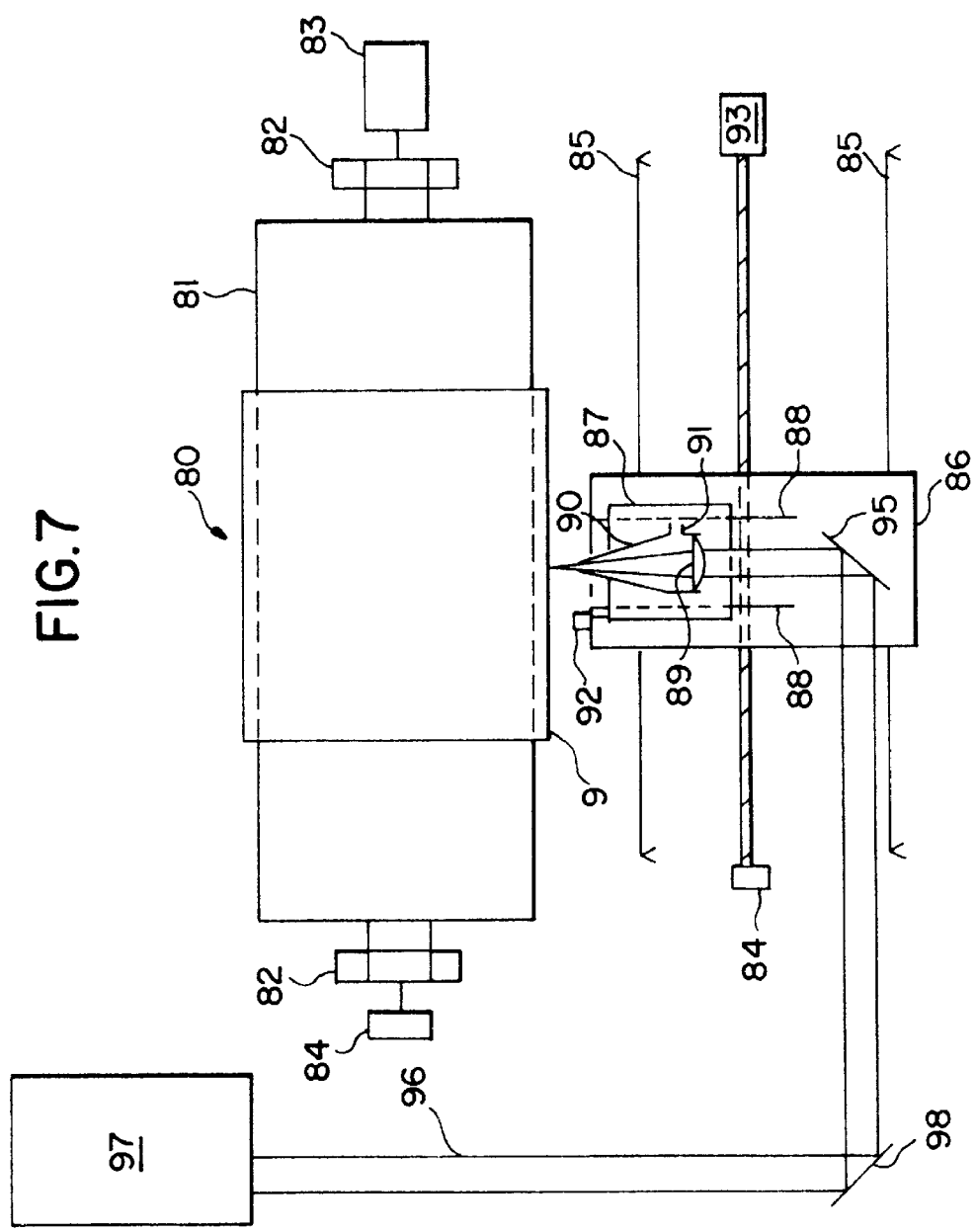

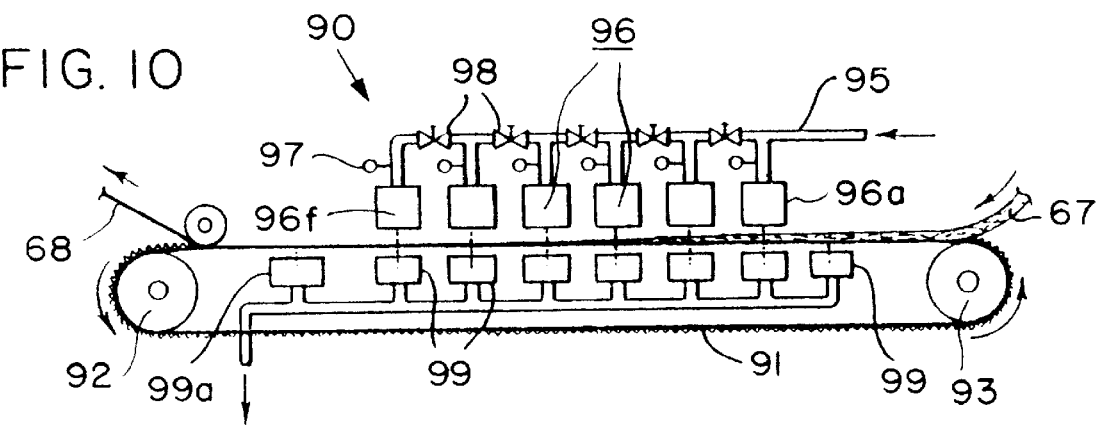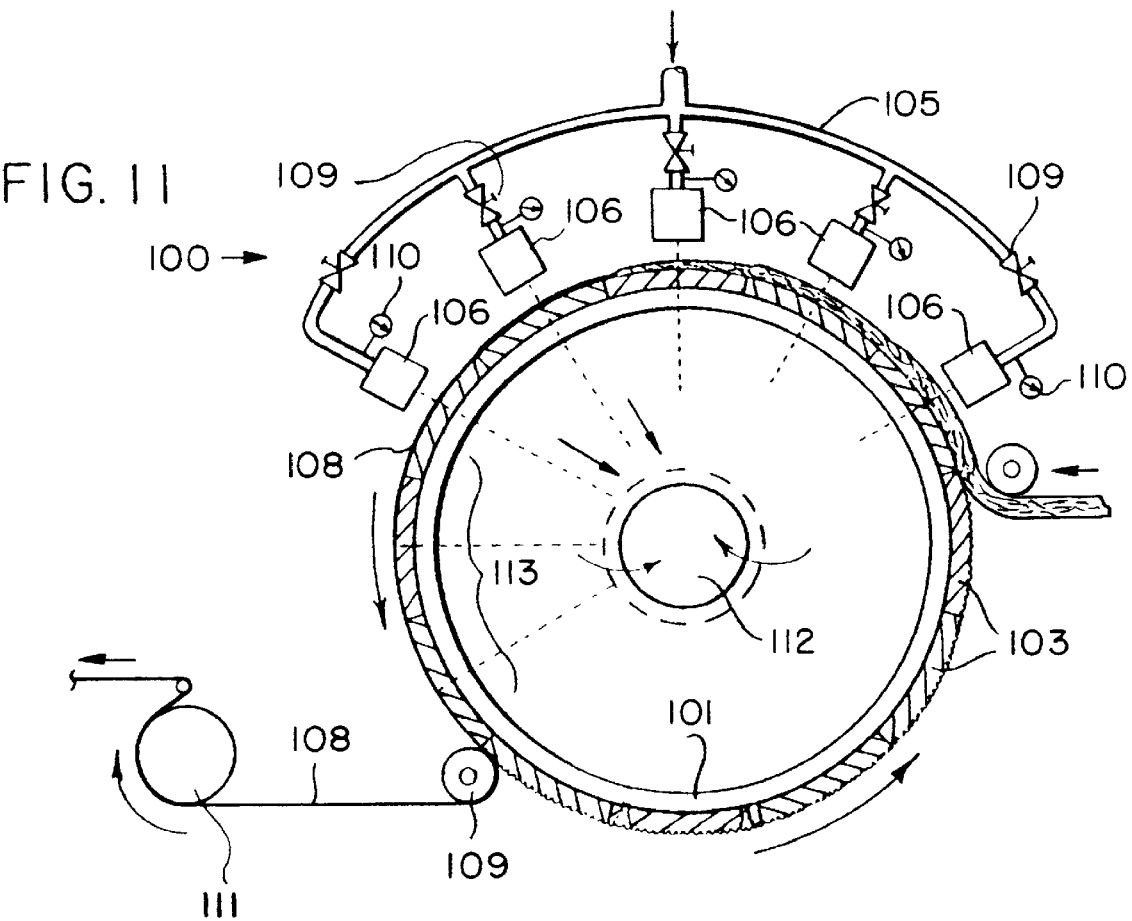

APPARATUS FOR PRODUCING AN APERTURED PLASTIC FILM HAVING A TRICOT TEXTURE

This application is a continuation of application Ser. No. 08/307,973 filed Sep. 16, 1994, now abandoned.

BACKGROUND OF THE INVENTION

Nonwoven fabrics have been used for a wide variety of applications for at least fifty years. Nonwoven fabrics are textile-like materials produced directly from a web of fibers so as to eliminate the many time consuming steps involved in converting staple length fibers into woven or knitted goods. In one method of making a nonwoven fabric, a web of fibers is produced, e.g. by carding or air laying techniques, and the fibrous web is then strengthened by the application thereto of a polymeric binding agent. In another method of making a nonwoven, the fibrous web is subjected to fluid forces which serve to entangle the fibers, thus providing strength to the finished material. Nonwoven fabrics are inherently porous structures, i.e. they comprise pores resulting from the overlapping and intersecting of their constituent fibers. These pores allow for the passage of fluids such as air and water or aqueous solutions. In addition, nonwoven fabrics may be made so as to have good softness, drapeability, and tactile impression. Owing to their desirable characteristics, nonwovens have been employed as facing materials for absorbent products such as disposable diapers, sanitary napkins, incontinent devices, wound dressings and the like.

More recently, efforts have been made to produce porous or liquid-permeable facing materials for absorbent products by using plastic films as the starting materials. For example, it is known to produce an apertured plastic film by placing a heated thermoplastic sheet material on a patterned perforated surface and applying a vacuum thereto. The vacuum pulls the softened sheet material through the perforations, thereby causing the film to rupture and form apertures.

U.S. Pat. No. 3,929,135 to Thompson et al. discloses perforated topsheet materials for absorptive devices such as sanitary napkins, incontinent pads, bandages and the like. These topsheet materials are constructed from liquid impervious materials such as low density polyethylene and comprise a plurality of tapered capillaries each of which has a base opening in the plane of the top sheet and an apex opening which is remote from the plane of the top sheet. The tapered capillaries disclosed by Thompson et al. are preferably provided in the form of a frustum of a conical surface and have an angle of taper of from about 10° to 60°.

U.S. Pat. No. 4,324,246 to Mullane et al. discloses an apertured formed film having a caliper of less than about 0.030 inch (0.075 cm), an open area of at least 35% and a plurality of apertures at least 75% of which have an equivalent hydraulic diameter (EHD) of at least 0.025 inch (0.064 cm). The apertured formed film disclosed by Mullane is useful as a topsheet for disposable absorbent products of the type mentioned above.

U.S. Pat. No. 4,839,216 to Curro et al. discloses a debossed and perforated plastic material produced by providing a starting film on a perforated forming surface and applying an unconstrained liquid stream to the upper surface of the starting film. The liquid stream has sufficient force and mass flux to cause the film to be deformed toward the forming surface, such that the material acquires a substantial three-dimensional conformation, and to cause perforations to be created therein.

European Patent Application 0 304 617 in the name of Kao Corporation discloses a covering sheet for a sanitary article. The covering sheet comprises an opaque, hydrophobic film having land portions and recesses, said recesses being formed to have a bottom portion and side walls. The side walls have a slanting part which is provided with an opening such that the slanting part is not covered by the land portion. This patent states that the opening is always exposed to sight when it is looked down at.

U.S. Pat. No. 4,690,679 discloses an apertured film comprising a first layer of a first polymeric film and a second layer of a second polymeric film. Apertured films wherein the apertures have average equivalent circular diameters ranging from about 0.010 inches (0.0254 cm) to about 0.030 inches (0.0762 cm) are disclosed as being useful as covering materials for absorbent products.

Other patents relating to apertured films and methods and apparatus for making the same include U.S. Pat. No. 3,632,269 to Doviak, et al. and U.S. Pat. No. 4,381,326 to Kelly.

Tricot knit fabrics are durable, soft and drapable. The tricot fabric structure provides high quality perception, good aesthetics, and luxurious appeal.

No apertured film in the market today has an appearance and tactile impression similar to tricot knit fabrics. A tricot-like film would be desirable as a covering material for a variety of disposable absorbent products.

SUMMARY OF THE INVENTION

The present invention is directed to an apertured plastic film having a tricot-like texture. The apertured film of the present invention comprises a stretchable thermoplastic polymeric material having a plurality of wales, a plurality of sloped side walls extending from the wales and a plurality of clusters of irregular micro-holes that are defined by a network of fiber-like elements. Each cluster of irregular micro-holes is connected between at least two of the sloped side walls. The plurality of wales extends longitudinally in a first direction which is transverse to a plurality of rows of undulating ribs. The rows of undulating ribs have a network of wales connected to opposite sides of the ribs. The sloped side walls extend at variable depths from the wales.

The apertured film of the present invention has an appearance and tactile impression characteristics similar to those found in tricot knit fabrics. The film is lint-free and has excellent softness. It permits efficient transport of fluids and is suitable for use as a cover material for disposable absorbent products.

BRIEF DESCRIPTION OF THE DRAWINGS

FIG. 4 is an exploded perspective view of the starting plastic film and a topographical support backing member on which the starting film is positioned during processing.

FIG. 7 is a schematic view of the apparatus for making the topographical support member.

FIG. 8 is a pixel by pixel diagram of an aperture pattern for making a topographical support member.

FIG. 10 is a diagrammatic view of one type of apparatus for producing apertured film of the present invention.

FIG. 11 is a diagrammatic view of a preferred apparatus for producing apertured film of the present invention.

DETAILED DESCRIPTION OF THE INVENTION

Figure 1:
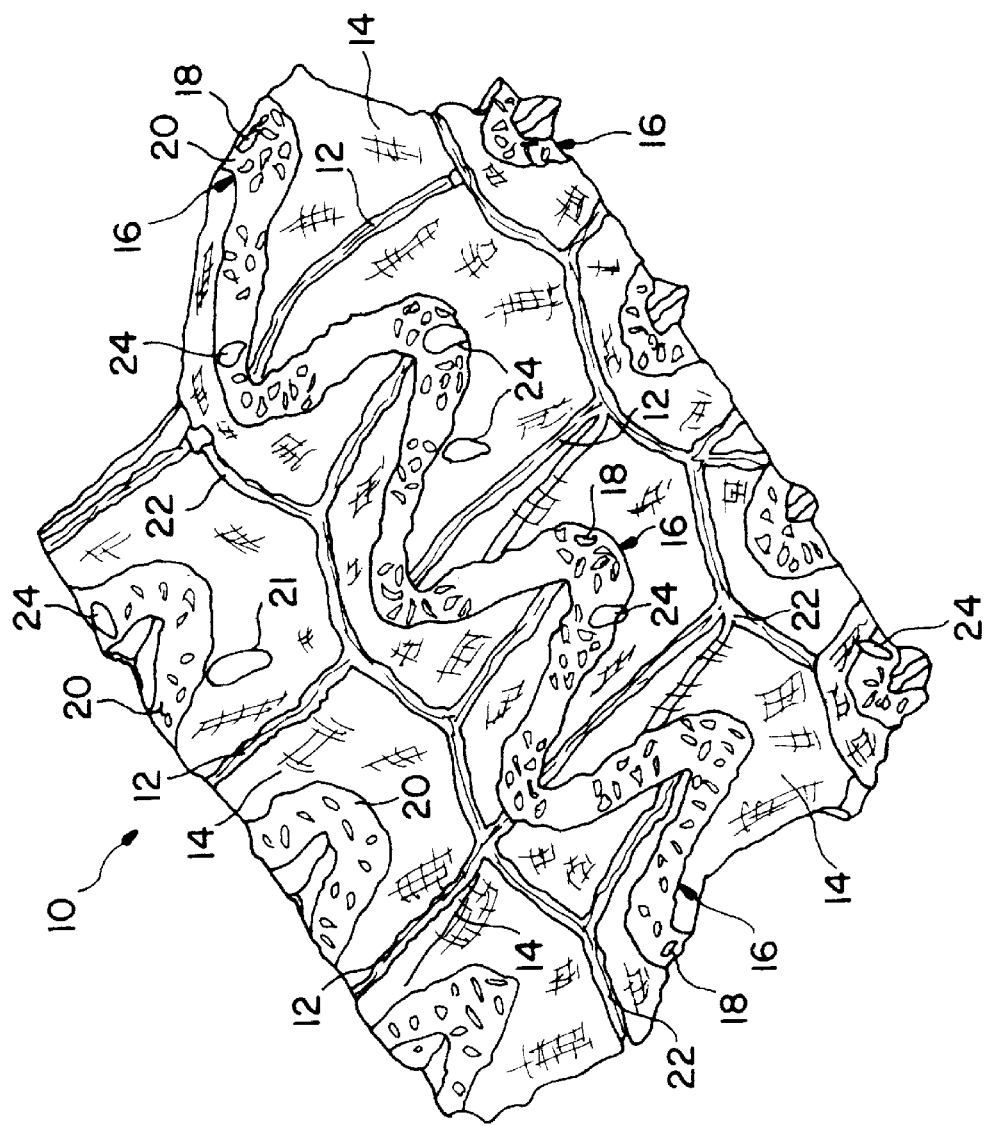
FIG. 1 is a perspective view of a portion of the apertured tricot-like plastic film of the present invention.
Figure 2:
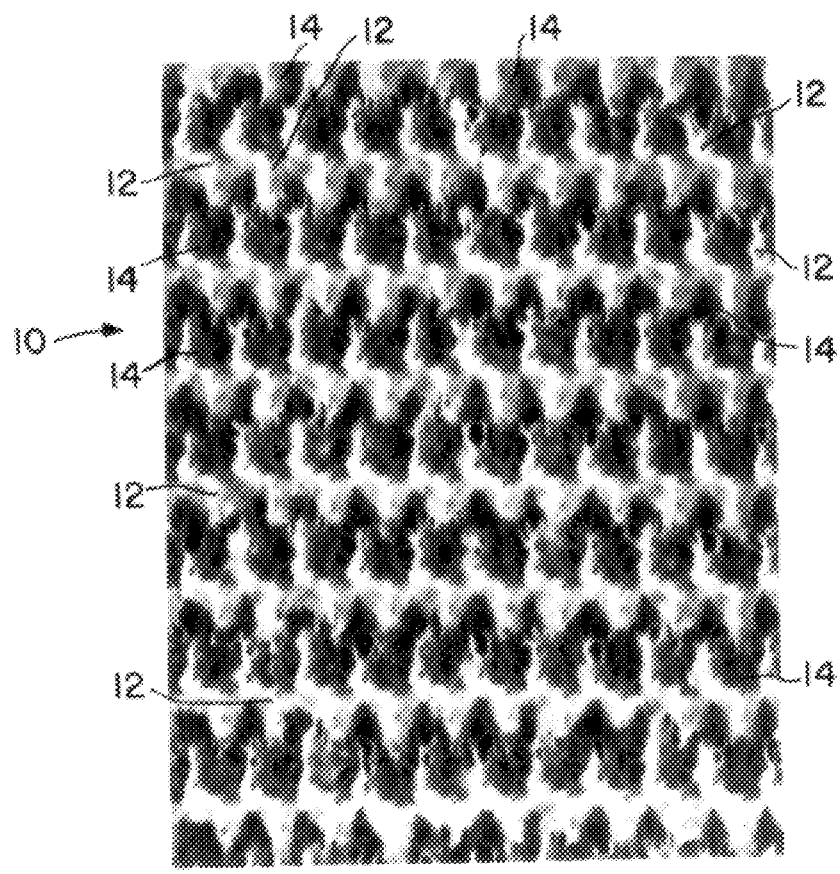
FIG. 2 is a photomicrograph plan view of the apertured tricot-like plastic film of the present invention.

Referring now to the drawings, FIG. 1 is a perspective view and FIG. 2 is a photomicrograph of an apertured plastic film having a tricot-like texture in accordance with the present invention.

The film 10 has a plurality of wales or ridges 12. The ridges 12 have sloped side walls 14 extending from the ridges to clusters 16 of irregular micro-holes 18 defined by a network of fiber-like elements or fibrils 20. The clusters 16 of micro-holes 18 are connected by the fibrils 20 between at least two of the sloped side walls 12. The fibrils 20 are drawn or stretched portions of the film that are formed during the manufacturing process. Extending in a transverse direction to the ridges 12 are a plurality of undulating ribs 22 that are substantially free of holes. As can be seen from FIGS. 1 and 2, the rows of undulating ribs 22 have a network of the wales 12 branching off from opposite sides of the ribs 22. The sloped side walls 14 extend from the wales 12 at variable depths. In addition, the side walls 14 are non-uniform in shape. The film 10 also includes a plurality of macro-holes 24 randomly dispersed throughout the film. The area of the macro-holes 24 is substantially larger than the area of the micro-holes 18.

The apertured tricot-like plastic film 10 shown in FIGS. 1 and 2 essentially consists of four levels or planes. The first plane is comprised of the plurality of wales 12, the second plane comprises the sloped side walls 14, the third plane comprises the cluster of irregular holes 18 with fibrils 20 between them, and the fourth plane comprises of apertured side walls 14 with variable depths.

Figure 3:
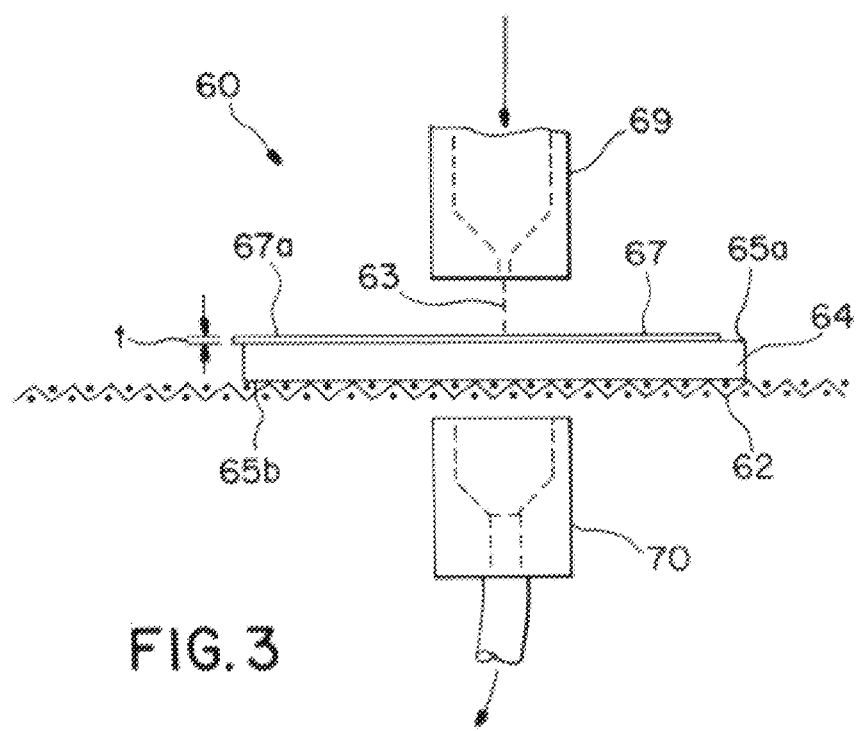
FIG. 3 is a schematic view of apparatus for producing apertured film of the present invention.

FIG. 3 is a schematic view showing an apparatus for making apertured plastic films of the present invention. Apparatus 60 comprises a movable conveyor belt 62 and a backing member 64, placed on top of the belt 62, to move with the belt. The backing member 64 has a plurality of openings (not shown in FIG. 3) disposed therein, said openings running through the thickness of the backing member 64 from its upper surface 65a to its lower surface 65b. The backing member 64 also has a predetermined topographical design that in combination with a pattern of apertures produces tricot-like characteristics in the apertured film.

Placed on top of the backing member 64 is a thin, continuous, uninterrupted starting film 67 of thermoplastic polymeric material. This starting film may be vapor permeable or vapor impermeable; it may be embossed or unembossed; it may, if desired, be corona-discharge treated on one or both of its major surfaces or it may be free of such corona discharge treatment. The stretchable film may comprise any thermoplastic polymeric material including, by way of example, polyolefins, such as polyethylene (high, linear low or low density) and polypropylene; copolymers of olefins and vinyl monomers, such as copolymers of ethylene and vinyl acetate or vinyl chloride; polyamides; polyesters; polyvinyl alcohol and copolymers of olefins and acrylate monomers such as copolymers of ethylene and ethyl acrylate and EMA (ethylenemethylacrylate). Starting film comprising mixtures of two or more such polymeric materials may also be used. The machine direction (MD) and cross direction (CD) elongation of the starting film to be apertured should be at least 100% as determined according to ASTM Test No. D-882 as performed on a Instron test machine run at a jaw speed of 50 inches/minute (127 cm/minute). The thickness of the starting film (i.e. the film to be apertured) is preferably uniform and may range from about 0.5 to 3 mils or about 0.0005 inch (0.0013 cm) to about 0.003 inch (0.076 cm). Co-extruded films can be used as can films which have been modified, e.g. by treatment with a surface active agent. The starting film can be made by any known technique such as casting, extrusion or blowing. Preferably a 1 mil micro-embossed film comprising a blend of linear low density polyethylene (LLDPE) and low density polyethylene (LDPE) is used.

Situated above starting film 67 is a manifold 69 for applying a fluid 63, preferably water, to the upper surface 67a of the starting film as said film, supported on backing member 64, is moved with conveyor belt 62. The water may be applied at varying pressures. Disposed beneath the conveyor belt is a vacuum manifold 70 for removing water which is directed onto upper surface 67a of starting film 67 as it passes under manifold 69.

In operation, starting film 67 is placed on backing member 64 and the film and backing member are passed back and forth under manifold 69 a number of times until the desired apertured film is produced.

Manifold 69 comprises a plurality of holes which may range in number from about 30 per lineal inch to about 100 per lineal inch. Preferably, the number of holes in the manifold ranges from about 35 per lineal inch to about 50 per lineal inch. The holes are preferably circular in configuration and have diameters ranging from about 0.003 inch (0.0076 cm) to about 0.01 inch (0.0254 cm), preferably 0.005 inch (0.0127 cm) to 0.007 inch (0.018 cm). After the starting film and backing member are passed under manifold 69 a number of times, the application of the water is stopped and the application of vacuum is continued to assist in dewatering the resulting apertured film of the invention. The apertured film is removed from the backing member and dried by any convenient technique such as the application thereto of a warm air flow or by solvent extraction.

FIG. 4 is an exploded perspective view of certain parts, i.e. starting film 67 and to topographical support or backing member 64, described earlier herein in conjunction with FIG. 3. As mentioned earlier, starting film 67 comprises a thermoplastic polymeric material or mixture of two or more such polymeric materials and, as illustrated in FIG. 4, the film may be embossed or unembossed. A portion 75 of starting film 67 comprising embossments 76, and a portion 77 of unembossed film 67 are shown in the upper portion of FIG. 4.

The backing or topographical support member 64 comprises a body 65 having a top surface 66 and bottom surface 67. Disposed in a predetermined pattern across top surface 66 is an array of peaks 68 separated by valleys 69. A plurality of drainage apertures 70 extending through the support member are disposed in a pattern in the member 64. In this embodiment, each drainage aperture 70 is surrounded by a cluster of six peaks 68 and six valleys 69.

The drainage apertures 70 are tapered, or "bell mouthed", having a larger diameter at the top surface of the support member than the bottom surface. Lines 71 are drawn tangent to opposed points on walls 72 one hole radius below top surface 66. The angle 73 formed by lines 71 must be controlled relative to the thickness 74 of the support member 64 to produce the intended result. A suitable angle can be established without undue experimentation. For example, if the angle is too great, the apertures 70 will be too small and insufficient drainage will be provided. If the angle is too small, there will be very few or no peaks and valleys.

The center-to-center spacing of adjacent apertures in the repeating pattern is of similar importance. The peaks 68 and valleys 69 are created by the intersection of the tapered somewhat conical apertures 70. If the center-to-center spacing of the apertures were greater than the major diameter of aperture 70 at the top surface 66, no intersection would result, and the member would be a smooth, flat top surface with conical apertures disposed throughout. When the center-to-center spacing of adjacent apertures is less than the aperture diameters measured along that center-to-center line, the conical surfaces intersect forming a valley. As shown in FIG. 4, the sections of the apertures just below the valleys are in the shape of truncated cones.

Figure 5:
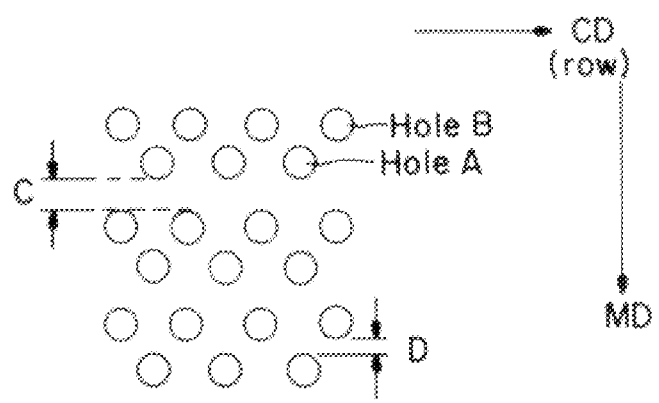
FIG. 5 is a diagram of one pattern of apertures of the backing member for producing the films of the present invention.

FIG. 5 is a diagram showing an example of one pattern of drainage apertures 70 used for a topographical support member. In this exemplary embodiment, there are two sizes of openings that are used to make up pairs of apertures in rows in the cross direction. The pairs are staggered in the machine direction (MD). The pairs are made up of a row of holes having a size A and a row of holes having a size B, where A is larger than B. The spacing C between pairs of A, B rows is greater than the spacing D between the A and B rows.

Figure 6:
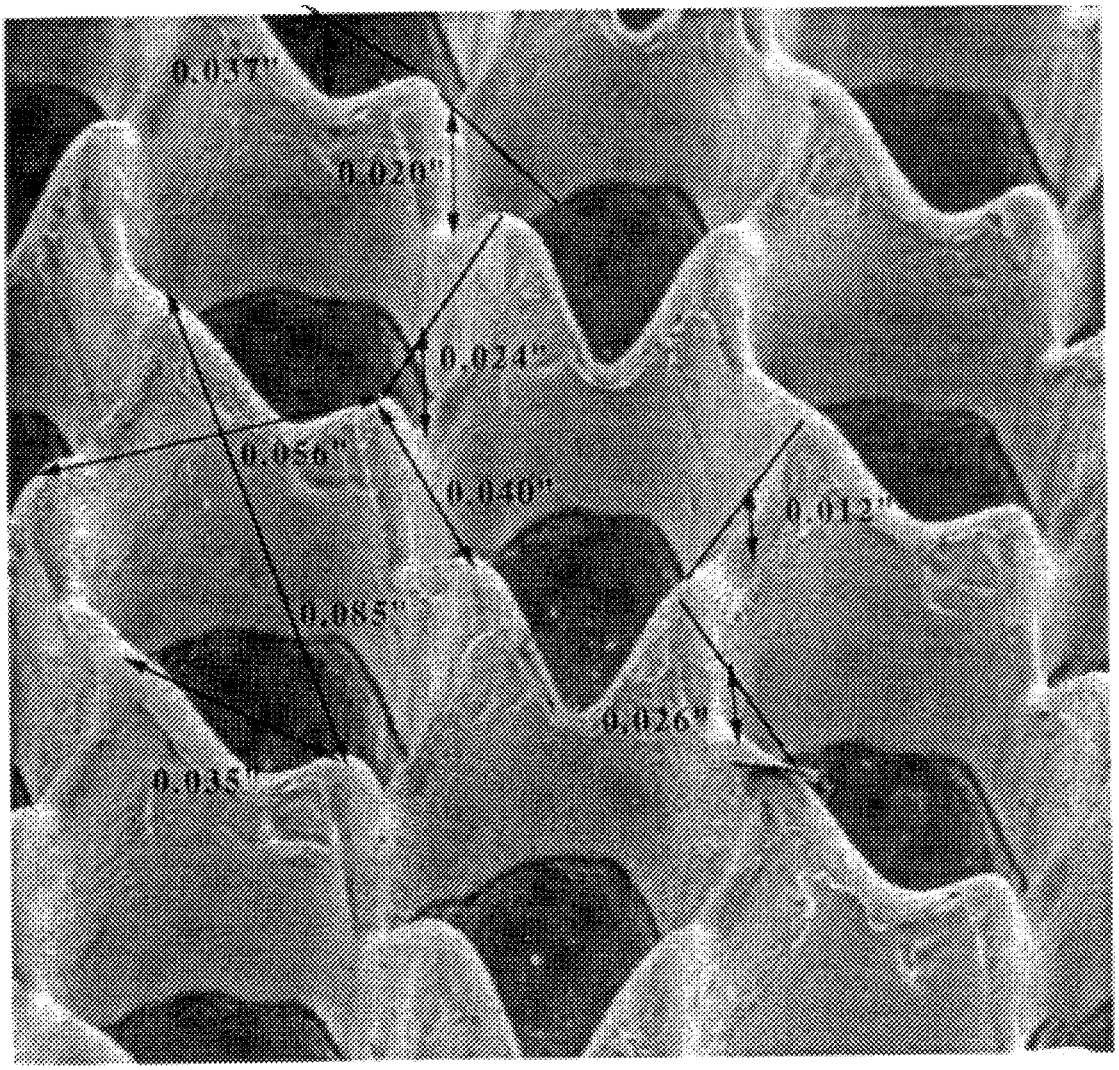
FIG. 6 is a digitized image of a topographical support member made with the aperture pattern of FIG. 5.

FIG. 6 is a digitized image of the forming member 64 shown in FIG. 4 that was fabricated using the hole pattern of FIG. 5. The holes of sizes A and B are shown with their respective dimensions of peak to valley heights and peak-to-peak spacing.

A preferred apparatus for producing the topographical support member of FIG. 4 is shown in FIG. 7. The starting material for the support member may be any desired shape or composition. The topographical support member preferably comprises acetal; acrylic will also perform satisfactorily. In addition, the preferred shape of the starting material is a thin wall, cylindrical, preferably seamless, tube that has been relieved of residual internal stresses. As will be described later, the cylindrical shape accommodates the preferred apparatus for producing the apertured films of the invention.

Tubes manufactured to date for use in forming support members are 2 to 6 feet in diameter and have a length ranging from 2 to 16 feet. The wall thickness is nominally ¼ inch. These sizes are a matter of design choice.

A starting blank tubular workpiece 80 is mounted on an appropriate arbor, or mandrel 81 that fixes it in a cylindrical shape and allows rotation about its longitudinal axis in bearings 82. A rotational drive 83 is provided to rotate mandrel 81 at a controlled rate. Rotational pulse generator 84 is connected to and monitors rotation of mandrel 81 so that its precise radial position is known at all times.

Parallel to and mounted outside the swing of mandrel 81 is one or more guide ways 85 that allow carriage 86 to traverse the entire length of mandrel 81 while maintaining a constant clearance to the top surface 9 of tube 80. Carriage drive 93 moves the carriage along guide ways 85, while carriage pulse generator 94 notes the lateral position of the carriage with respect to support member 80. Mounted on the carriage is focusing stage 87. Focusing stage 87 is mounted in focus guide ways 88 and allows motion orthogonal to that of carriage 86 and provides a means of focusing lens 89 relative top surface of tube 80. Focus drive 92 is provided to position the focusing stage 87 and provide the focusing of lens 89.

Secured to focusing stage 87 is the lens 89, which is secured in nozzle 90. Nozzle 90 has means 91 for introducing a pressurized gas into nozzle 90 for cooling and maintaining cleanliness of lens 89.

Also mounted on the carriage 86 is final bending mirror 95, which directs the laser beam 96 to the focusing lens 89. Remotely located is the laser 97, with optional beam bending mirrors 98 to direct the beam to final beam bending mirror 95. While it would be possible to mount the laser 97 directed on carriage 86 and eliminate the beam bending mirrors, space limitations and utility connections to the laser make remote mounting far preferable.

When the laser 97 is powered, the beam 96 emitted is reflected first off beam bending mirror 98, then final beam bending mirror 95, which directs it to lens 89. The path of laser beam 96 is configured such that, if lens 89 were removed, the beam would pass through the longitudinal center line of mandrel 81.

With lens 89 in position, the beam is focused below, but near the top surface 9 of tube 80. Focusing the beam below the top of surface is identified as "defocusing" the laser beam relative to the surface of the tube.

While this invention could be used with a variety of lasers, the preferred laser is a fast flow $CO_2$ laser, capable of producing a beam rated at up to 2500 watts. This process is in no way dependent on such a high power laser, as support surfaces have been successfully drilled with a slow flow $CO_2$ laser limited to 50 watts.

When focusing lens 89 passes beam 96, it concentrates the energy near the center of the beam. The rays are not bent through a single point, but rather a spot of small diameter. The point of smallest diameter is said to be the focus or focal point. This occurs at a distance from the lens said to be the focal length. At lengths either shorter or greater than the focal length, measured spot sizes will be greater than the minimum.

The sensitivity to focus position is inversely proportional to focal length. Minimum spot size is directly proportional to focal length. Therefore, a short focal length lens can achieve a smaller spot size but must be more accurately positioned and is affected dramatically by surface run-out. Longer focal length lenses are more forgiving of target positioning, but can only achieve somewhat larger spot sizes. Thus, in addition to the power distribution contributing to the tapered top portion of the drilled aperture, the defocusing of the beam below the surface also contributes to the angle and length of the taper, and hence the shape and size of the peaks and valleys.

In order to fabricate a support member, an initial focusing step must be performed. Once a blank tubular workpiece 80 is positioned on the mandrel 81, the laser is pulsed briefly and the mandrel rotated slightly between pulses such that a series of small depressions is produced. The focus stage 87 is then moved with respect to the mandrel center line to change the focus position and another series of depressions is produced. Typically a matrix of 20 rows of 20 depressions each is drilled. The depressions are examined microscopically, and the column of smallest depressions identified. This is established as the reference diameter for top surface 9 of the blank tubular workpiece 80 at which the beam was focused.

A desired pattern is selected, such as the one shown in FIG. 5. The pattern is examined to determine the number of repeats that will be required to cover the circumference of the workpiece and complete the surface without an obvious seam. Similarly, the advance along the longitudinal axis of the tubular workpiece per repeat and total number of repeats is established. These data are entered into a computer control for operating the laser drilling machine.

In operation, the mandrel, with the tubular workpiece mounted thereon, is rotated in front of the lens. The carriage is motored so that the first aperture position corresponds with the focal point of the lens 89. The focus stage is motored inward, placing the focal point inside the interior of the material to be drilled. The laser is then pulsed, with some combination of pulse power level and duration. As seen in FIG. 4, the diameter of aperture 70 at the top surface 66 is considerably larger than the diameter of the aperture at the lower surface 67. In order to achieve the desired topographical configuration, two factors need to be measured and controlled. First, the degree with which the lens is focused into the interior of the workpiece increases the cone angle 73, and second, increasing the power level or pulse duration increases the depth and diameter. Once an aperture of the proper diameter and taper is achieved, the rotational drive and carriage drive can be indexed to reposition the support member such that the next intended hole position corresponds to the focal point. The process is then repeated until the entire pattern has been drilled. This technique is known as "percussion" drilling.

If the laser selected is of sufficient power, the mandrel and carriage do not need to be stopped during the laser pulse. The pulse can be of such short duration that any movement of the workpiece during the drilling process is inconsequential. This is known in the trade as "fire-on-the-fly" drilling.

If the laser can recover rapidly enough, the workpiece can be rotated at a fixed speed and the laser pulsed once to create each hole. In a pattern such as the one shown in FIG. 5, the laser would normally be pulsed to produce a complete column, the carriage indexed to the next column position and the beam pulsed for the next series of apertures.

One problem that may occur depending on the type of material and density of the pattern of apertures, is the introduction of a large amount of heat into a small area of the forming surface. Gross distortion, and the loss of pattern registration may result. Under some conditions, major dimensional changes of the part results, and the surface is neither cylindrical nor the right size. In extreme cases, the tube may crack.

A preferred embodiment of the present invention, which eliminates this problem, uses a process called defocused raster scan drilling.

In this approach, the pattern is reduced to the smallest rectangular repeat element 41 as depicted in FIG. 8. This repeat element contains all of the information required to produce the pattern in FIG. 5. When used like a tile and placed both end-to-end and side-by-side, an overall pattern is the result.

This repeat element is further divided into a grid of smaller rectangular units or "pixels" 42. Though typically square, for some purposes, it is more convenient to employ pixels of unequal proportions.

Each column of pixels represents one pass of the workpiece past the focal position of the laser. This column is repeated as many times as is required to reach completely around support member 80. Each pixel where the laser is intended to create a hole is black. Those pixels where the laser is turned off are white.

To begin drilling at the top of the first column of pixels in FIG. 8, while the mandrel is turning at a fixed rate, the laser is turned on, maintained at a constant power level for 11 pixels and then switched off. These pixels are counted by the rotational pulse generator 84 in FIG. 7. The laser remains off for the next 14 units. This laser off/on sequence is repeated for the first revolution, at which point the mandrel is back to starting position, carriage drive 93 has repositioned the carriage one unit and the computer is ready to do column 43a.

During column number 43a, the laser has a shorter "on time" (now 9 units) and longer "off time" (now 16 units). The total number of on and off times is a constant based on the pattern height.

This process is repeated until all of the columns have been used over an entire revolution each; in the case of FIG. 8, there were 15 revolutions of the mandrel. At this point, the process returns to the instructions in column 43.

Note that in this approach, each pass produces a number of narrow cuts in the material, rather than a large hole. Because these cuts are precisely registered to line up side-by-side and overlap somewhat, the cumulative effect is a hole. In the pattern of FIG. 8, each hexagonal hole 44 actually requires 7 passes separated by a complete revolution, distributing the energy around the tube and minimizing local heating.

If, during this drilling operation, the lens was focused at the top surface of the material, the result would be hexagonal holes with reasonably parallel walls. The combination of raster scan drilling with the defocused lens approach, however, produces the forming surface of FIG. 4.

In the present invention, the apertures 70 are quite small and numerous. Typical patterns range from 800 to 1400 apertures per square inch.

Figure 9:
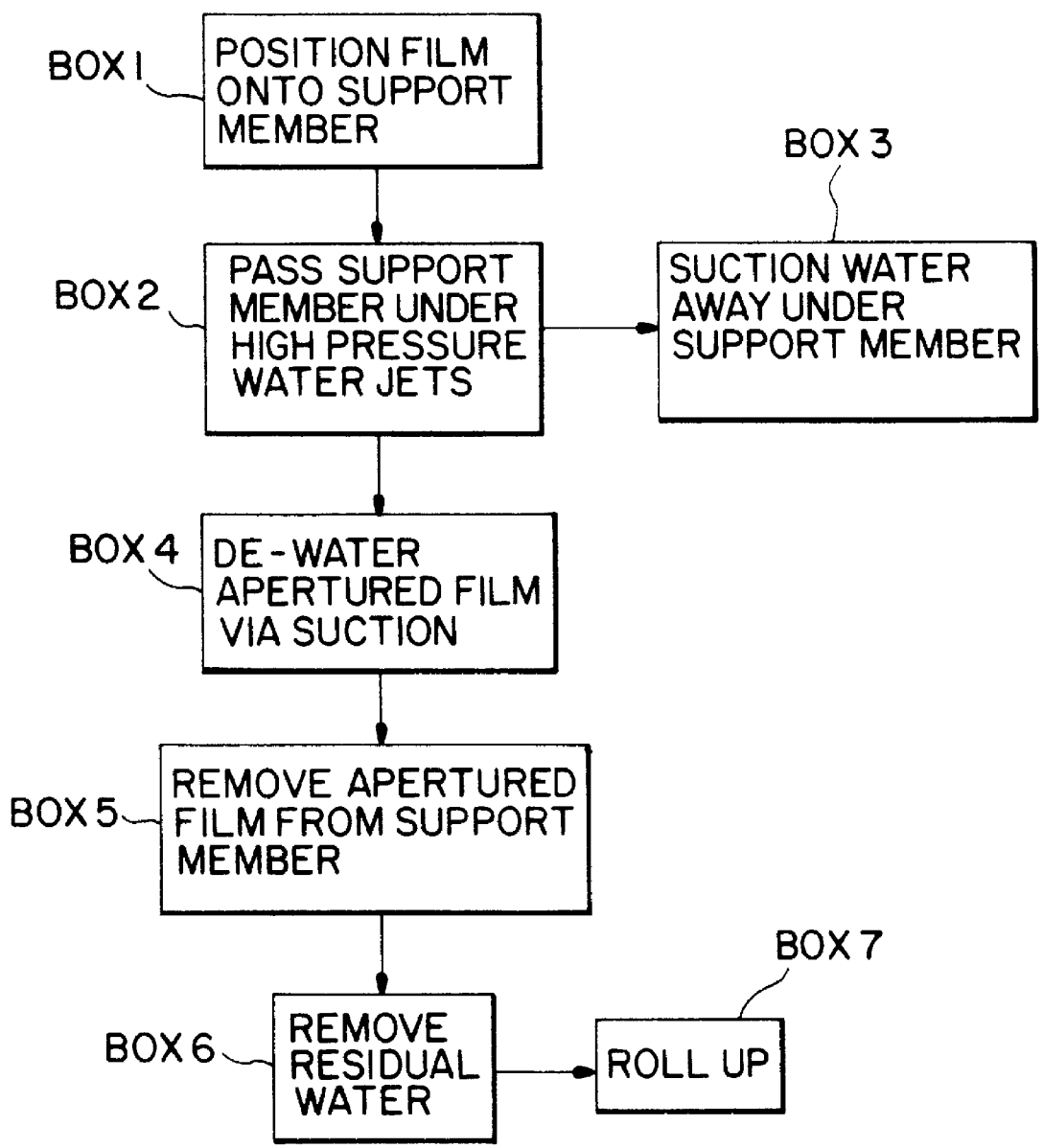
FIG. 9 is a block diagram of the process steps for producing the film of the present invention.

FIG. 9 is a block diagram showing the several steps in the process for producing the novel apertured films of the present invention. The first step in the process is to position a piece of thin, stretchable film of thermoplastic polymer materials on a support member (Box 1). The support member with the stretchable film thereon is passed under high pressure fluid ejecting nozzles (Box 2). The preferred fluid is water. The water is transported away from the support member, preferably using a vacuum (Box 3). The film is dewatered, suction being preferred for this purpose (Box 4). The de-watered apertured film is removed from the support member (Box 5). Residual water is removed from the apertured film, e.g. by applying a stream of air thereto (Box 6). The apertured film is then rolled up to await use as is or as a structural component of another product such as a sanitary napkin, disposable diaper or wound dressing (Box 7).

FIG. 10 is a diagrammatic view of an apparatus for continuously producing the apertured films of the present invention. Apparatus 90 comprises a backing member provided in the form of a conveyor belt 91. Conveyor belt 91 is continuously moved in a counterclockwise direction about a pair of spaced apart rollers 92, 93 as is well-known. Disposed above conveyor belt 91 is a fluid supply manifold 95 connecting a plurality of lines or groups 96 of orifices. Each group 96 of orifices includes at least one row of very small diameter holes, there being thirty or more of such holes per lineal inch in each row. Manifold 95 is equipped with pressure gauges 97 and control valves 98 for regulating the fluid pressure in each line or group of orifices. Means (not illustrated in the drawings) are provided for supplying water at an elevated temperature to manifold 95. Disposed beneath each orifice line or group is a suction member 99 for removing excess water during processing and to keep the aperturing zone from flooding. The starting film 67 to be formed into the apertured film 68 of the invention is fed to the conveyor belt comprising the backing member. The starting film passes under the group 96 of orifices where it is exposed to the columnar streams of water being ejected from the orifices. The pressure of the water columns being ejected from the individual groups 96 of orifices can be set by pressure control valves 98 to any desired pressure. The pressure of the water supplied to the groups 96 of orifices should be at least about 500 psig and may range up to 1500 psig or even higher. In the process for making apertured films of the present invention, it is preferred that the individual groups 96 of orifices eject water at the same pressure. Though six fluid supplying groups of orifices are shown in FIG. 10, the number of groups 96 of orifices is not critical, but will depend on the thickness of the starting film, the speed of the conveyor belt, the pressures employed, the number of rows of orifices in each group 96 of orifices, etc. After passing between the columnar water jets and suction manifold 99, the apertured film 68 passes over an additional suction slot 99a to remove excess processing water therefrom. The conveyor belt comprising the backing member may be made from relatively rigid material and may comprise a plurality of slats. Each slat extends across the width of the conveyor and has a lip on one side and a slat engages the lip of an adjacent slat to allow for movement between adjacent slats and to allow for these relatively rigid slat members to be employed in the conveyor configuration shown in FIG. 10. Alternatively, the backing member may be a woven screen having high points which support the film and low points into which the film is moved during processing.

Referring to FIG. 11, there is shown a preferred apparatus for making apertured films of the present invention. Apparatus 100 comprises a rotatable drum 101. The drum has a honey-comb structure to allow for the passage of fluids therethrough, rotates in a counterclockwise direction and carries a backing member in the form of an elongated cylinder or sleeve 103 placed over its outer surface. Disposed about a portion of the periphery of the drum is a manifold 105 connecting a plurality of orifice strips 106 for applying water to a stretchable thermoplastic starting film 107 carried on the outer surface of sleeve 103. Each orifice strip comprises a row of very fine uniform circular holes. The diameter of these holes should range from approximately 0.005 inch (0.0127 cm) to 0.010 inch (0.0254 cm). There may be as many as 50 or 60 holes per lineal inch or more if desired. Water is directed under pressure through the orifices, forming columnar streams which impinge on the upper surface of the starting film in a contact or aperturing zone below the orifice strips. The distance from the orifice strips to the upper surface of film 107 being processed is about 0.75 inch (1.90 cm.). The pressure of the water supplied to the orifice strips is controlled by pressure control valves 109, the pressure being indicated by pressure gauges 110. The drum is connected to a pump 112 to which a vacuum may be applied to aid in removing water so as to keep the aperturing zone from flooding. In operation, the starting film 107 is placed on the backing member 103 and passed counter-clockwise under the water ejecting orifice strips 106. As film 107 passes underneath the orifice strips, it is formed into the apertured film of the invention.

The apertured tricot-like plastic film of the present invention has a micro-hole size that is under 25 mils equivalent hydraulic diameter (EHD) and equivalent circular diameter (ECD). The ECD data are obtained from an image analyzer and is calculated in accordance with the following formula:

$$ECD = \sqrt{\frac{4A}{\pi}},$$

where A is equal to the area of the micro-hole. EHD is calculated from the measured area and perimeter of each micro-hole according to the formula:

$$EHD = 4\frac{A}{P},$$

where A equals the mirco-hole area and P equals the micro-hole perimeter. The average ECD ranges from about 2 to 7 mils with the preferred average being 5 mils. The ECD coefficient of variation (COV) ranges from 50 to 70%. The EHD COV is at least 40%. COV is determined from the formula:

$$COV = \frac{SD}{mean} \times 100\%,$$

where SD is the standard deviation. The number of micro-holes per square inch ranges from about 4,000 to 7,000 with the preferred number being about 6,000 micro-holes per square inch. The area of the micro-holes ranges from about 4000 to 7000 square mils. The open area of the film may be as low as 1%. The thickness of the film ranges from about 10 to 20 mils with the preferred bulk being 15 mils. The number of wales ranges from 500 to 6,000 per square inch. The width of the fiber-like elements ranges from 1 to 10 mils with the preferred range being from 1 to 5 mils. The length of the fiber-like elements ranges from about 10–500 mils.

Example 1

An apertured film of the present invention was made by processing a starting film on the apparatus of FIG. 11. The starting film comprised a 40:60 (wt %) blend of commercially available low density polyethylene and linear low density polyethylene. The starting film had a thickness of 0.8 mil and was embossed with a diamond pattern having 165 lines per inch. Only 3 of the orifice strips 106 in the apparatus of FIG. 11 were employed. Water at 160° F. was supplied to the three orifice strips at a pressure of 1350 psig. The line speed of the apparatus was 50 yards/minute. The sleeve 103 had the topographical configuration shown in FIG. 4. The resulting apertured film has an open area of 10%. The average ECD of the micro-holes in the final film was 5 mils. The COV of the ECD of the micro-holes was 58%. The Frazier air permeability of the apertured film was 350 cubic feet/minute/sq. ft. of film.

Example 2

Example 1 was repeated except that the starting film had a thickness of 0.95 mil and the pressure at which water was supplied to the three orifice strips was 1200 psig. The resulting apertured film had an open area of 5%. The average ECD of the micro-holes in the film was 3 mils. The COV of the ECD of the micro-holes was 62%. There were 6,300 micro-holes per square inch and all of the micro-holes had an EHD under 25 mils.

The films produced in the above examples were lint free films suitable for use as a wiping cloth or pouch cover. In addition, the film structure did not have interstices to entrap fluid which provides clean/dry properties. The films had good aesthetics, fabric feel, efficient fluid transport and softness.

The apertured films of the present invention may be used as facing materials for absorbent products such as disposable diapers, sanitary napkins, wound dressings, incontinent devices and the like.

When used as covering materials for sanitary napkins, it is preferred that the micro-holes of the apertured thermoplastic films of the present invention be sufficient in number to provide an open area ranging from about 1 to 15%, with the number of larger-sized holes preferably being minimized. It is preferred that at least fifty percent (50%) of the micro-holes comprising the film have EHD's ranging between 0.5 and 25 mils. The COV of EHD of the micro-holes is preferably at least 50%. Preferably, at least seventy-five percent (75%) of the micro-holes have areas less than 400 square mils and the coefficient of variation of micro-hole area should be at least 100%.

Figure 12:
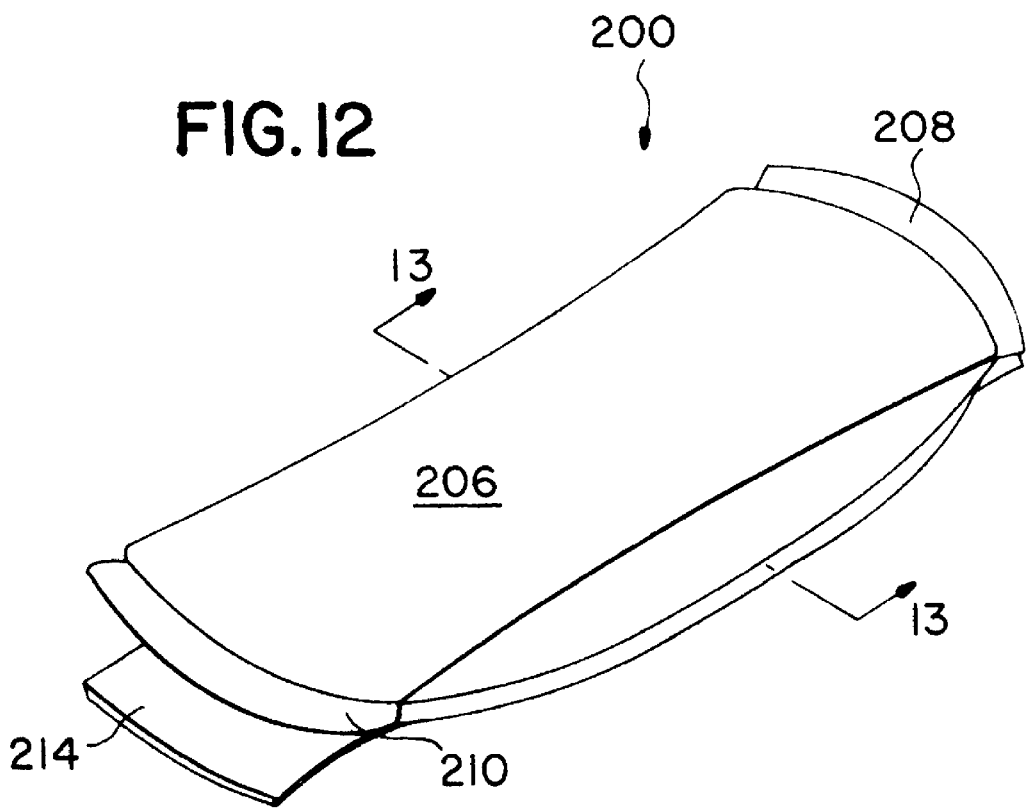
FIG. 12 is a perspective view of a sanitary napkin comprising the apertured film of the present invention.
Figure 13:
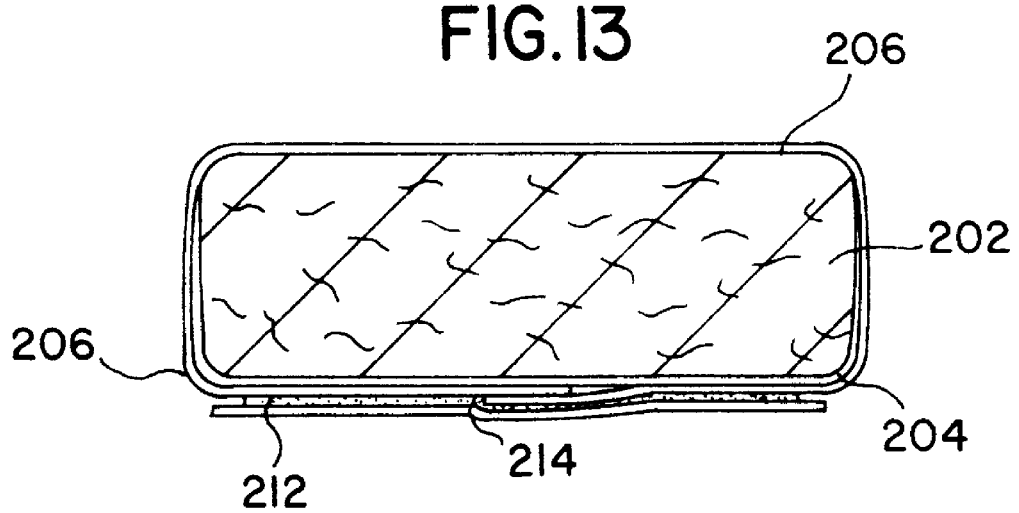
FIG. 13 is a partial sectional view taken along lines 13—13, FIG. 12.

Referring to FIGS. 12 and 13, there is shown a sanitary napkin 200 comprising an absorbent core 202 of wood pulp fibers, a thin, fluid-impermeable barrier film 204 and a covering material 206 which may be any of the apertured films of the invention. Preferably, the covering material has the structure shown and described herein with reference to FIGS. 1 and 2. Barrier film 204, which may comprise, e.g. a thin film of polyethylene, contacts the lower surface of absorbent core 202 and runs part way up the longitudinal sides of the absorbent core. Covering material 206 has a length somewhat longer than the length of the absorbent core and is wrapped around the absorbent core and barrier film as shown in FIG. 13. The longitudinal edges of the cover material are overlapped and sealed together on the lower surface of the napkin in the usual manner. In the embodiment illustrated, the cover material is sealed to itself at the ends 208, 210 of the sanitary napkin. As illustrated in FIG. 13, sanitary napkin 200 has a layer of adhesive 212 for adhering the napkin to the undergarment of the user. Adhesive 212 is protected prior to use by a removable release strip 214.

While several embodiments and variations of the present invention are described in detail herein, it should be apparent that the disclosure and teachings of the present invention will suggest many alternative designs to those skilled in the art.

What is claimed is:

1. An apparatus for producing an apertured film having a tricot texture, the apparatus comprising:

a backing support member comprising a rotatable hollow drum having a cylindrical side wall and a pattern of apertures extending through the side wall from a top surface to a bottom surface, the top surface having a topography comprising a plurality of peaks and valleys, each of said apertures being surrounded by a cluster of the peaks and valleys formed in the sidewall, the apertures each having a section just below the valleys which has the shape of a truncated cone whereby the aperture diameter at the top surface of said section is greater than the aperture diameter at the bottom surface of said section, the pattern of apertures, peaks, and valleys being adapted to produce a film having a tricot texture;

means for positioning a stretchable thermoplastic polymer film on the apices of the peaks on the top surface of the drum;

means located outside the drum for projecting adjacent fluid streams simultaneously against said film and then against the peaks and then through the apertures and into the drum;

means for rotating the drum while said fluid is being projected against the top surface;

means disposed inside the drum to remove the fluid from the top surface of the drum; and means for removing the apertured film having a tricot texture from the top surface of the drum.

2. The apparatus as claimed in claim 1, wherein the cluster of peaks and valleys surrounding each aperture comprises individual peaks having varying heights and shapes, and individual valleys having varying depths and shapes.

* * * * *